US00PP13953P39

(12) United States Plant Patent
Crocker

(10) Patent No.: US PP13,953 P3
(45) Date of Patent: Jul. 8, 2003

(54) *PLUMBAGO AURICULATA* NAMED 'MONITE'

(75) Inventor: Brad Alan Crocker, Aliseo Viejo, CA (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 09/826,222

(22) Filed: Apr. 5, 2001

(65) Prior Publication Data

US 2002/0148019 P1 Oct. 10, 2002

(51) Int. Cl.[7] ..... A01H 5/00

(52) U.S. Cl. ..... Plt./226

(58) Field of Search ..... Plt./226

*Primary Examiner*—Bruce R. Campell

*Assistant Examiner*—Susan B. McCormick

(57) ABSTRACT

A new and distinct selection of Plumbago shrub, denominated as *Plumbago auriculata* named 'Monite' characterized by its unique combination of longer bloom season of a floriferous habit of white flowers with larger and wider petals and a more dense compact growth habit.

1 Drawing Sheet

BACKGROUND

This invention relates to a new and distinct selection of *Plumbago auriculata*, which is native to Southern Africa, and a member of the Leadwort family. The new variety, *Plumbago auriculata* cv. 'Monite' resulted from a naturally occurring, whole plant mutation which was discovered in May of 1999 in a cultivated planting of *Plumbago auriculata* 'Monott' (U.S. Plant Pat. No. 7,822). 'Monite' exhibited a white flower in #1 nursery containers in Azusa, Calif. The 'Monite' selection differs from 'Monott' by possessing a white flower versus the rich blue flower of 'Monott'. 'Monite' differs from other Plumbago plants by its combination of floriferous habit of white flowers and larger and wider petals and a more dense compact growth habit.

The new plant has been asexually reproduced by cuttings since its discovery in 1999 in Azusa, Calif. Through extensive asexual propagation of this plant and observation, it has been established that the plant is true to type and the novel, exceptional characteristics of this new plant are fixed and stable and reliably passed on to progeny through asexual reproduction.

SUMMARY

*Plumbago auriculata* cultivar 'Monite' possesses a white flower. Other white flowering Plumbago plants do exist, however; the individual flowers do not exhibit the larger size and fullness associated with the overlapping flower petals of cultivar 'Monite'.

The compact growth habit of cultivar 'Monite' sets this plant apart from other Plumbago plants which are generally sprawling, mounding plants with a height of 6–8 feet and 8–10 foot spread. The growth habit of cultivar 'Monite' is slightly smaller than 'Monott'.

The cultivar 'Monite' typically will bloom for eight to nine months of the year in Southern California commencing bloom before even the early cultivar 'Monott'. Comparison of other Plumbago plants demonstrate cultivar 'Monite' has the propensity to conspicuously grow less and flower more when grown under similar conditions.

BOTANICAL DESCRIPTION

Figure 1:
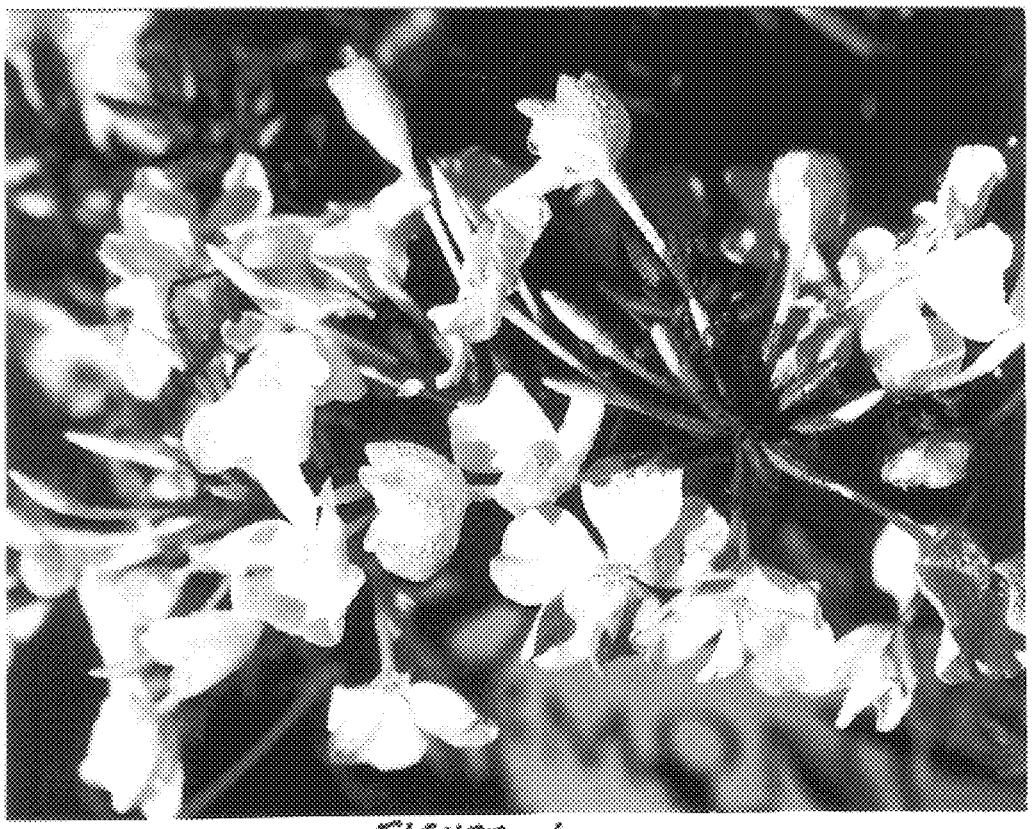
FIG. 1 photograph exhibits a close up of the inflorescence of cultivar 'Monite'.
Figure 2:
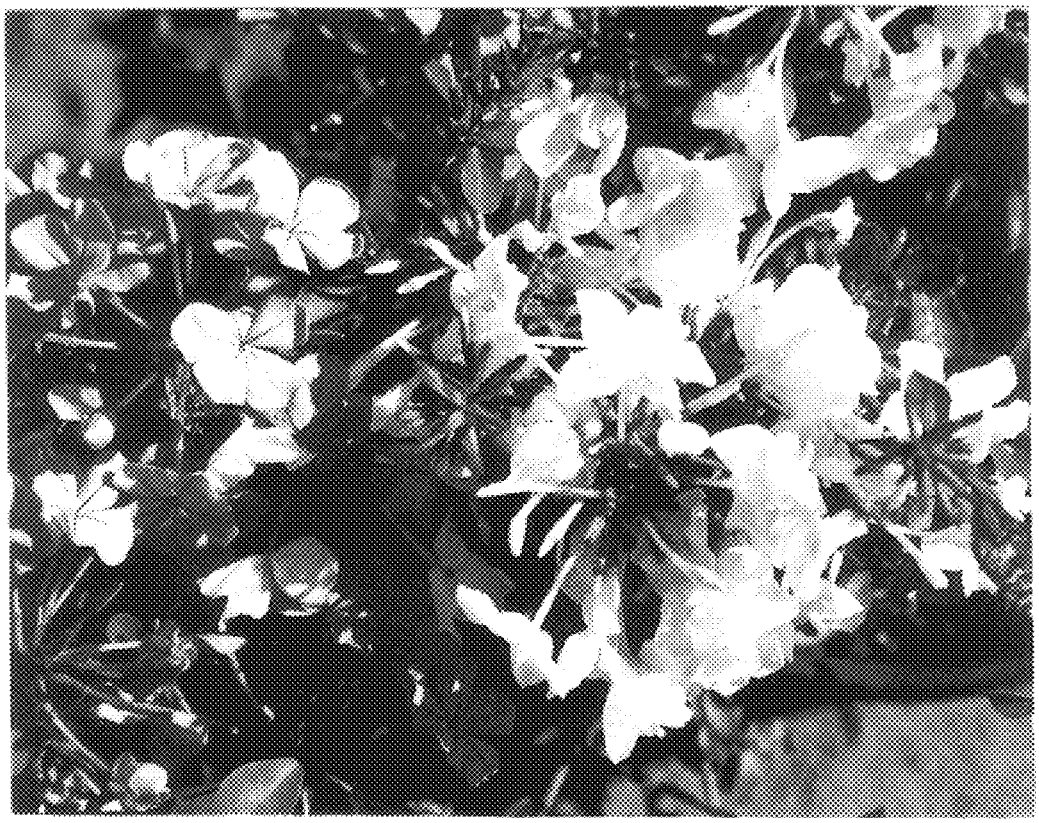
FIG. 2 photograph shows the comparison of cultivar 'Monite' on the right and cultivar 'Monott' on the left and the similarity of flower size and contrast of flower color.

Below is a detailed description of *Plumbago auriculata* cultivar 'Monite'. Color terminology is from The Royal Horticultural Society Colour Charts. Measurements are based on five year old plants grown in Southern California.

Overall habit: Mounding shrub.

Overall size: Maximum height from soil surface to top of foliage ranges from 120 cm to 150 cm. Maximum width of the plant ranges from 120 cm to 150 cm.

Flowering time in Southern California: Flowering commences in early March and continues until November.

Root initiation: Six to eight weeks.

Flower:

*Arrangement*.—Terminal, spike like racemes.

*Lastingness of bloom*.—Averaging 2 to 3 days.

*Corolla diameter*.—Averaging 2.5 to 3 cm in width.

*Corolla color*.—White Group 155D.

*Corolla*.—Tubular with 5 parted lobes. Tube: typically 3 cm in length; 2 mm in width. Lobes: slightly overlapping, obovate in shape, acute base averaging 1.5 cm long and 1 cm wide, prominent midrib, slightly depressed. Texture: thin, glabrous.

*Calyx*.—Tubular, 5 parted at tip. Color: Green Group 141C. Size: averaging 1.3 cm in length, 3 mm in width. Surface: upper half of calyx with stalked glands, Greyed-Red Group 180C. Bracts: 3 at base, 6–7 mm long and 2 mm wide, color Green Group 141C.

*Stamens.*—5 in number, adhering to within throat arising above corolla tube. Anthers: length averaging 2 mm. width: less than 1 mm. color: Violet-Blue 92B. Filaments: length averaging 3 cm. width: less than 1 mm, very slender. color: White Group 155D.

*Pistil.*—Averaging 2 cm in length. Color: White Group 155D.

Fragrance: None detected.

Fruit: To date not observed.

Foliage:

*Size.*—Length: ranges from 3.5 cm to 6.5 cm. Width: ranges from 1 cm to 2 cm.

*Shape.*—Overall: oblong to oblong — spatulate to obtuse. Base: auricled, wrapping around stem, narrowly acute. Tip: shortly mucronate.

*Margin.*—Entire, slightly undulate.

*Color.*—Mature upper surface: Yellow Green Group 146A. Mature lower surface: Yellow Green Group 146B. Juvenile upper surface: Yellow Green Group 146B. Juvenile lower surface: Yellow Green Group 146C.

*Texture.*—Thin, glabrous.

*Arrangement.*—Alternate.

*Venation.*—Pattern: pinnate, craspedrome. Upper surface: Yellow-Green Group 146C. Lower surface: Yellow-Green Group 146D.

Branchlets:

*Juvenile.*—Lightly ribbed, 2–3 mm in diameter. color: Yellow Green Group 146B.

*Mature.*—3 mm and larger in diameter. color: Red-Purple Group 59C mixed with Yellow Green Group 146B.

*Length.*—Varies from 60 cm.

*Length of internode.*—Varies from 2.5 cm to 6 cm dependent upon age and sun exposure on branch.

Disease resistance: As is typical of this species, 'Monite' cultivar exhibited a strong resistance to disease under normal growing conditions.

Heat and drought hardiness: When established in the landscape 'Monte' is very tolerant of dry conditions and reflected and dry heat.

Winter hardiness: As is typical of this species, will tolerate to a 25 degree Fahrenheit temperature.

I claim:

1. A new and distinct *Plumbago auriculata* plant named 'Monite' substantially as herein shown and described.

* * * * *